(12) United States Patent
Zhong et al.

(10) Patent No.: US 11,676,734 B2
(45) Date of Patent: Jun. 13, 2023

(54) PATIENT THERAPY MANAGEMENT SYSTEM THAT LEVERAGES AGGREGATED PATIENT POPULATION DATA

(71) Applicant: MEDTRONIC MINIMED, INC., Northridge, CA (US)

(72) Inventors: Yuxiang Zhong, Arcadia, CA (US); Pratik Agrawal, Porter Ranch, CA (US); Michael P. Stone, Long Beach, CA (US); Kevin E. Velado, Northridge, CA (US); Sinu Bessy Abraham, Gallatin, TN (US); Siddharth Arunachalam, Northridge, CA (US); Valerie Dormant, Santa Monica, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 885 days.

(21) Appl. No.: 16/189,899

(22) Filed: Nov. 13, 2018

(65) Prior Publication Data
US 2019/0148024 A1 May 16, 2019

Related U.S. Application Data

(60) Provisional application No. 62/586,653, filed on Nov. 15, 2017.

(51) Int. Cl.
*G16H 80/00* (2018.01)
*G16H 10/60* (2018.01)
(Continued)

(52) U.S. Cl.
CPC .......... *G16H 80/00* (2018.01); *A61B 5/0022* (2013.01); *A61B 5/14532* (2013.01);
(Continued)

(58) Field of Classification Search
CPC ................................................ G06Q 50/22–24
See application file for complete search history.

(56) References Cited

U.S. PATENT DOCUMENTS

| 4,755,173 A | 7/1988 | Konopka et al. |
| 5,391,250 A | 2/1995 | Cheney, II et al. |
| | (Continued) | |

FOREIGN PATENT DOCUMENTS

| WO | WO-2017083480 A1 * | 5/2017 | ............. G16H 10/20 |
| WO | WO2017083480 A1 | 5/2017 | |

*Primary Examiner* — Robert W Morgan
*Assistant Examiner* — Edward B Winston, III
(74) *Attorney, Agent, or Firm* — Weaver Austin Villeneuve & Sampson LLP

(57) ABSTRACT

A computer-implemented therapy management system is operated to collect patient data associated with medical device users. Treatment of the users is managed by healthcare professionals (HCPs), which include a customer HCP and a plurality of non-customer HCPs. The system receives a first set of attributes for a first individual patient or a first group of patients under care of the customer HCP, and a second set of attributes for a second individual patient or a second group of patients. The system identifies a first set of patient records associated with the customer HCP that satisfy the received first attributes, and a second set of patient records that satisfy the received second attributes, and compares patient outcomes from the first set of records against patient outcomes from the second set of records. A comparative therapy report is generated and communicated to a client device associated with the customer HCP.

20 Claims, 6 Drawing Sheets

(51) Int. Cl.
  *G16H 20/17* (2018.01)
  *A61B 5/00* (2006.01)
  *A61B 5/145* (2006.01)
  *A61M 5/00* (2006.01)
  *G16H 50/20* (2018.01)
  *A61M 5/172* (2006.01)
  *A61M 5/142* (2006.01)
  *G16H 20/00* (2018.01)
  *G16H 50/30* (2018.01)
  *G16H 40/67* (2018.01)

(52) U.S. Cl.
  CPC ............. *A61B 5/743* (2013.01); *A61M 5/003* (2013.01); *A61M 5/142* (2013.01); *A61M 5/1723* (2013.01); *G16H 10/60* (2018.01); *G16H 20/00* (2018.01); *G16H 20/17* (2018.01); *G16H 50/20* (2018.01); *A61B 5/0004* (2013.01); *A61B 5/486* (2013.01); *A61B 5/4839* (2013.01); *A61B 5/7225* (2013.01); *A61B 5/746* (2013.01); *A61B 5/7435* (2013.01); *A61M 2205/3584* (2013.01); *A61M 2205/502* (2013.01); *A61M 2205/52* (2013.01); *G16H 40/67* (2018.01); *G16H 50/30* (2018.01)

(56) References Cited

U.S. PATENT DOCUMENTS

| | | | |
|---|---|---|---|
| 5,485,408 | A | 1/1996 | Blomquist |
| 5,505,709 | A | 4/1996 | Funderburk et al. |
| 5,522,803 | A | 6/1996 | Teissen-Simony |
| 5,665,065 | A | 9/1997 | Colman et al. |
| 5,800,420 | A | 9/1998 | Gross et al. |
| 5,807,375 | A | 9/1998 | Gross et al. |
| 5,925,021 | A | 7/1999 | Castellano et al. |
| 5,954,643 | A | 9/1999 | Van Antwerp et al. |
| 6,017,328 | A | 1/2000 | Fischell et al. |
| 6,186,982 | B1 | 2/2001 | Gross et al. |
| 6,246,992 | B1 | 6/2001 | Brown |
| 6,248,067 | B1 | 6/2001 | Causey, III et al. |
| 6,248,093 | B1 | 6/2001 | Moberg |
| 6,355,021 | B1 | 3/2002 | Nielsen et al. |
| 6,379,301 | B1 | 4/2002 | Worthington et al. |
| 6,485,465 | B2 | 11/2002 | Moberg et al. |
| 6,544,212 | B2 | 4/2003 | Galley et al. |
| 6,554,798 | B1 | 4/2003 | Mann et al. |
| 6,558,351 | B1 | 5/2003 | Steil et al. |
| 6,591,876 | B2 | 7/2003 | Safabash |
| 6,641,533 | B2 | 11/2003 | Causey, III et al. |
| 6,659,980 | B2 | 12/2003 | Moberg et al. |
| 6,736,797 | B1 | 5/2004 | Larsen et al. |
| 6,749,587 | B2 | 6/2004 | Flaherty |
| 6,752,787 | B1 | 6/2004 | Causey, III et al. |
| 6,766,183 | B2 | 7/2004 | Walsh et al. |
| 6,801,420 | B2 | 10/2004 | Talbot et al. |
| 6,804,544 | B2 | 10/2004 | Van Antwerp et al. |
| 6,817,990 | B2 | 11/2004 | Yap et al. |
| 6,932,584 | B2 | 8/2005 | Gray et al. |
| 7,003,336 | B2 | 2/2006 | Holker et al. |
| 7,029,444 | B2 | 4/2006 | Shin et al. |
| 7,066,909 | B1 | 6/2006 | Peter et al. |
| 7,137,964 | B2 | 11/2006 | Flaherty |
| 7,303,549 | B2 | 12/2007 | Flaherty et al. |
| 7,399,277 | B2 | 7/2008 | Saidara et al. |
| 7,442,186 | B2 | 10/2008 | Blomquist |
| 7,602,310 | B2 | 10/2009 | Mann et al. |
| 7,621,893 | B2 | 11/2009 | Moberg et al. |
| 7,647,237 | B2 | 1/2010 | Malave et al. |
| 7,699,807 | B2 | 4/2010 | Faust et al. |
| 7,727,148 | B2 | 6/2010 | Talbot et al. |
| 7,785,313 | B2 | 8/2010 | Mastrototaro |
| 7,806,886 | B2 | 10/2010 | Kanderian, Jr. et al. |
| 7,819,843 | B2 | 10/2010 | Mann et al. |
| 7,828,764 | B2 | 11/2010 | Moberg et al. |
| 7,879,010 | B2 | 2/2011 | Hunn et al. |
| 7,890,295 | B2 | 2/2011 | Shin et al. |
| 7,892,206 | B2 | 2/2011 | Moberg et al. |
| 7,892,748 | B2 | 2/2011 | Norrild et al. |
| 7,901,394 | B2 | 3/2011 | Ireland et al. |
| 7,942,844 | B2 | 5/2011 | Moberg et al. |
| 7,946,985 | B2 | 5/2011 | Mastrototaro et al. |
| 7,955,305 | B2 | 6/2011 | Moberg et al. |
| 7,963,954 | B2 | 6/2011 | Kavazov |
| 7,977,112 | B2 | 7/2011 | Burke et al. |
| 7,979,259 | B2 | 7/2011 | Brown |
| 7,985,330 | B2 | 7/2011 | Wang et al. |
| 3,024,201 | A1 | 9/2011 | Brown |
| 8,100,852 | B2 | 1/2012 | Moberg et al. |
| 8,114,268 | B2 | 2/2012 | Wang et al. |
| 8,114,269 | B2 | 2/2012 | Cooper et al. |
| 8,137,314 | B2 | 3/2012 | Mounce et al. |
| 8,181,849 | B2 | 5/2012 | Bazargan et al. |
| 8,182,462 | B2 | 5/2012 | Istoc et al. |
| 8,192,395 | B2 | 6/2012 | Estes et al. |
| 8,195,265 | B2 | 6/2012 | Goode, Jr. et al. |
| 8,202,250 | B2 | 6/2012 | Stutz, Jr. |
| 8,207,859 | B2 | 6/2012 | Enegren et al. |
| 8,226,615 | B2 | 7/2012 | Bikovsky |
| 8,257,259 | B2 | 9/2012 | Brauker et al. |
| 8,267,921 | B2 | 9/2012 | Yodfat et al. |
| 8,275,437 | B2 | 9/2012 | Brauker et al. |
| 8,277,415 | B2 | 10/2012 | Mounce et al. |
| 8,292,849 | B2 | 10/2012 | Bobroff et al. |
| 8,298,172 | B2 | 10/2012 | Nielsen et al. |
| 8,303,572 | B2 | 11/2012 | Adair et al. |
| 8,305,580 | B2 | 11/2012 | Aasmul |
| 8,308,679 | B2 | 11/2012 | Hanson et al. |
| 8,313,433 | B2 | 11/2012 | Cohen et al. |
| 8,318,443 | B2 | 11/2012 | Norrild et al. |
| 8,323,250 | B2 | 12/2012 | Chong et al. |
| 8,343,092 | B2 | 1/2013 | Rush et al. |
| 8,352,011 | B2 | 1/2013 | Van Antwerp et al. |
| 8,353,829 | B2 | 1/2013 | Say et al. |
| 9,886,556 | B2 * | 2/2018 | Booth .................. G16H 20/60 |
| 2007/0123819 | A1 | 5/2007 | Mernoe et al. |
| 2008/0004507 | A1 * | 1/2008 | Williams, Jr. ......... A61B 5/055 600/300 |
| 2010/0160861 | A1 | 6/2010 | Causey, III et al. |
| 2013/0047113 | A1 | 2/2013 | Hume et al. |
| 2014/0088393 | A1 * | 3/2014 | Bernstein ............... G16H 50/20 600/365 |
| 2014/0324445 | A1 * | 10/2014 | Carlsgaard ............. G16H 40/67 705/2 |
| 2017/0053072 | A1 | 2/2017 | Agrawal et al. |
| 2017/0053552 | A1 * | 2/2017 | Zhong .................. A61B 5/7405 |
| 2017/0329933 | A1 * | 11/2017 | Brust ............... G06F 16/24575 |
| 2018/0040088 | A1 * | 2/2018 | Kanada ................. G06Q 10/103 |
| 2018/0052964 | A1 * | 2/2018 | Adelson ................ G16H 10/60 |
| 2020/0105380 | A1 * | 4/2020 | Ennist ................... G16H 10/60 |

* cited by examiner

US 11,676,734 B2

PATIENT THERAPY MANAGEMENT SYSTEM THAT LEVERAGES AGGREGATED PATIENT POPULATION DATA

CROSS-REFERENCE TO RELATED APPLICATION(S)

This application claims the benefit of U.S. provisional patent application Ser. No. 62/586,653, filed Nov. 15, 2017. The content of the referenced application is incorporated by reference herein.

TECHNICAL FIELD

Embodiments of the subject matter described herein relate generally to systems and methods for diabetes therapy management. More particularly, embodiments of the described subject matter relate to a computer-based tool that generates and communicates patient related information, such as glucose management recommendations, to end user devices.

BACKGROUND

Portable medical devices are useful for patients that have conditions that must be monitored on a continuous or frequent basis. For example, diabetics are usually required to modify and monitor their daily lifestyle to keep their blood glucose (BG) in balance. Individuals with Type 1 diabetes and some individuals with Type 2 diabetes use insulin to control their BG levels. To do so, diabetics are advised to routinely keep strict schedules, including ingesting timely nutritious meals, partaking in exercise, monitoring BG levels daily, and adjusting and administering insulin dosages accordingly.

The prior art includes a number of fluid infusion devices and insulin pump systems that are designed to deliver accurate and measured doses of insulin via infusion sets (an infusion set delivers the insulin through a small diameter tube that terminates at, e.g., a cannula inserted under the patient's skin). In lieu of a syringe, the patient can simply activate the insulin pump to administer an insulin bolus as needed, for example, in response to the patient's high BG level. A patient can monitor BG levels using a BG meter or measurement device and by using a continuous glucose sensor if so desired.

In practice, many processes and behaviors result in fluctuations in BG levels. Commonly recognized processes and factors impacting BG levels include food, exercise, disease (acute or chronic), medication (insulin, oral, etc.), and stress and sleep patterns, among others. Furthermore, behavioral and environmental factors such as the time of the day, attentiveness to therapy, and insulin pump maintenance, can provide additional quantitative indications of the underlying factors impacting glucose control. Current reporting tools available to diabetes patients and their caregivers are patient-specific in that they collect and analyze data in a way that is intended to address an individual patient's particular glycemic outcome.

Accordingly, it is desirable to have a system and related methodologies that support enhanced and more intelligent reporting to diabetes patients using an insulin infusion system. Furthermore, other desirable features and characteristics will become apparent from the subsequent detailed description and the appended claims, taken in conjunction with the accompanying drawings and the foregoing technical field and background.

BRIEF SUMMARY

A method of generating and communicating comparative therapy information for medical device users is disclosed. An exemplary embodiment of the method includes the steps of: collecting patient data associated with a plurality of medical device users, wherein treatment of the medical device users is managed by a plurality of healthcare professionals (HCPs), and the plurality of HCPs includes a customer HCP and a plurality of non-customer HCPs; receiving a first set of attributes for a first individual patient or a first group of patients under care of the customer HCP; receiving a second set of attributes for a second individual patient or a second group of patients; identifying, from the collected patient data, a first set of patient records associated with the customer HCP that satisfy the received first attributes; identifying, from the collected patient data, a second set of patient records that satisfy the received second attributes; comparing patient outcomes from the identified first set of patient records against patient outcomes from the identified second set of patient records; generating a comparative therapy report that indicates results of the comparing step; and communicating the comparative therapy report to a client device associated with the customer HCP.

A computer-implemented therapy management system is also disclosed here. An exemplary embodiment of the system includes: at least one processor device; and a non-transitory processor-readable medium operatively associated with the at least one processor device. The processor-readable medium stores executable instructions configurable to cause the at least one processor device to perform a method including the steps of: collecting patient data associated with a plurality of medical device users, wherein treatment of the medical device users is managed by a plurality of HCPs, and the plurality of HCPs includes a customer HCP and a plurality of non-customer HCPs; receiving a first set of attributes for a first individual patient or a first group of patients under care of the customer HCP; receiving a second set of attributes for a second individual patient or a second group of patients; identifying, from the collected patient data, a first set of patient records associated with the customer HCP that satisfy the received first attributes; identifying, from the collected patient data, a second set of patient records that satisfy the received second attributes; comparing patient outcomes from the identified first set of patient records against patient outcomes from the identified second set of patient records; generating a comparative therapy report that indicates results of the comparing step; and communicating the comparative therapy report to a client device associated with the customer HCP.

Also disclosed here is an exemplary embodiment of a system that includes: a computer-implemented therapy management system; a database system, associated with the therapy management system, to collect and maintain patient data associated with a plurality of medical device users, wherein treatment of the medical device users is managed by a plurality of HCPs, and the plurality of HCPs includes a customer HCP and a plurality of non-customer HCPs; and a computer-implemented user device communicatively coupled to the therapy management system, wherein the user device is associated with the customer HCP. The therapy management system is operative to: receive a first set of attributes for a first individual patient or a first group of patients under care of the customer HCP; receive a second set of attributes for a second individual patient or a second group of patients; identify, from the collected patient data, a first set of patient records associated with the customer HCP that satisfy the received first attributes; identify, from the collected patient data, a second set of patient records that satisfy the received second attributes; compare patient outcomes from the identified first set of patient records against patient outcomes from the identified second set of patient records; generate a comparative therapy report that indicates results of the comparing step; and communicate the comparative therapy report to the user device associated with the customer HCP.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
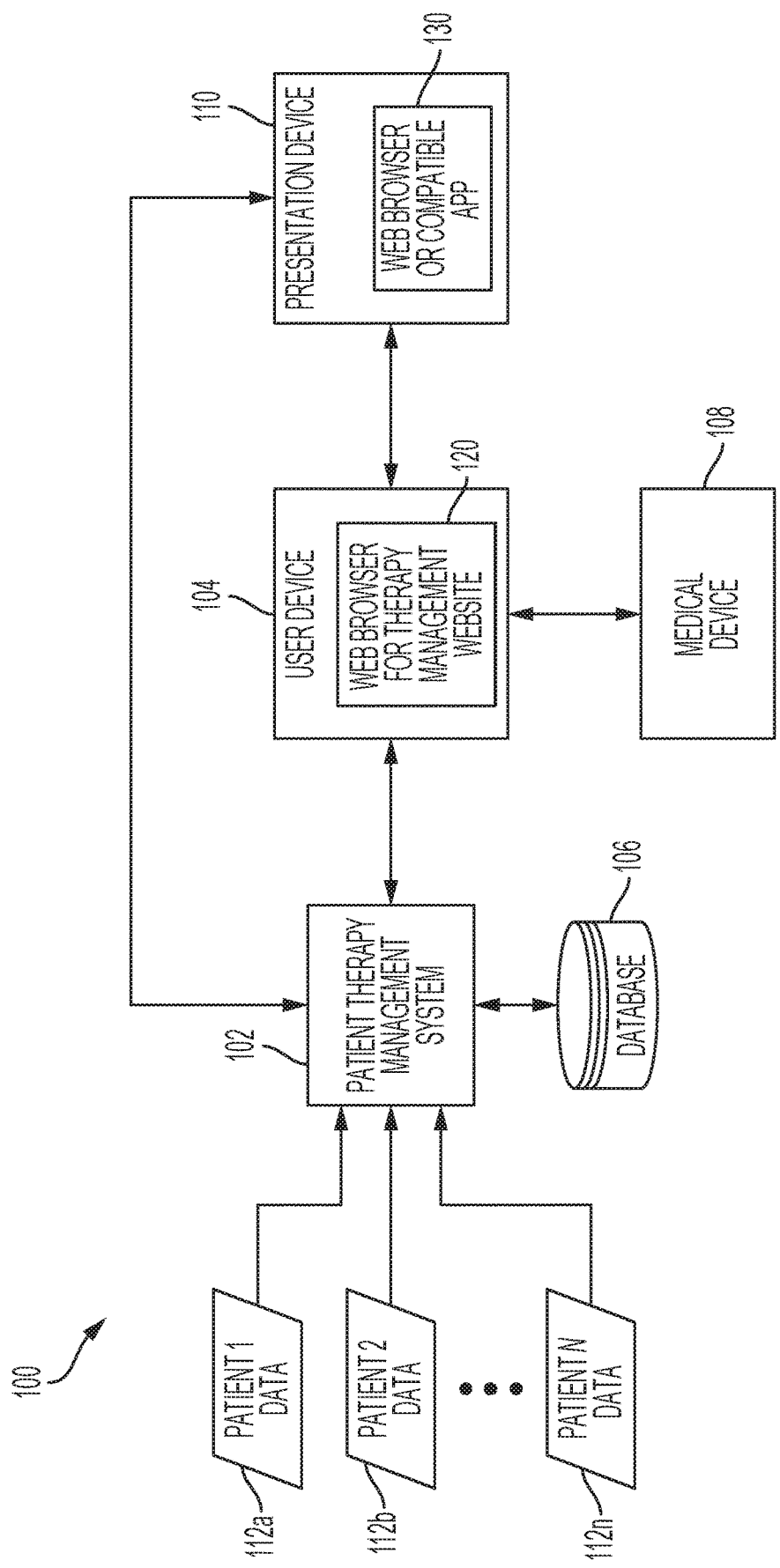
FIG. 1 is a simplified block diagram representation of an operating environment than includes a patient therapy management system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

When implemented in software, firmware, or processor-readable instructions, various elements of the systems described herein are essentially the code segments or instructions that perform the various tasks. In certain embodiments, the program or code segments are stored in a tangible processor-readable medium, which may include any medium that can store or transfer information. Examples of a non-transitory and processor-readable medium include an electronic circuit, a semiconductor memory device, a ROM, a flash memory, an erasable ROM (EROM), a floppy diskette, a CD-ROM, an optical disk, a hard disk, or the like.

The following description relates to a diabetes patient support system that generates and delivers therapy-related content to end users. Although not limited to any particular use case, the end users for the exemplary embodiment described here are healthcare professionals, caregivers, doctors, payors, etc. (rather than patients). That said, the system described here can be utilized to provide therapy-related content to patients if so desired. The exemplary embodiment disclosed herein is a cloud-based architecture in that most of the processor-intensive tasks are performed by one or more server systems that communicate with remotely located computer-based user devices. The disclosed system obtains and processes patient data for a population of different patients under the care of different physicians. Patient data can originate from various sources, including insulin infusion devices, continuous glucose sensor devices, mobile client devices, patient owned or operated computer systems, activity tracker devices, navigation or global positioning system (GPS) devices, etc. Aggregated patient data is processed and analyzed to generate therapy-related content that can be displayed on a website and/or via a web-based application.

An exemplary embodiment of the system described here can utilize an online (web browser based) application that serves as a diabetes therapy management tool. To this end, the system can be implemented with a website that provides population-based diabetes therapy recommendations, advice, and/or guidance to healthcare providers, doctors, caregivers, etc., for purposes of driving better glycemic outcomes. In accordance with certain implementations, the web-based tool provides physicians with valuable information (recommendations) for patients on insulin therapy, and enables physicians to make better informed decisions regarding the care of their patients, wherein at least some of those decisions are based on the analysis of patient data collected for a large population of patients. Actionable recommendations lead to better patient engagement and improve care efficiency. The healthcare professional is also provided with aggregated statistics related to patient behavior, glucose sensor patterns, alarm, and transmitter patterns. The web-based tool is an ideal platform to leverage machine learning algorithms to cluster patient population based on similar behavior and to help predict glycemic outcomes. As a practical business matter, the web-based application also plays a pivotal role in improving sales of related infusion pumps and glucose sensors, because certain advantageous features and functions can be highlighted by the web-based application (such as predictive low glucose management, hybrid closed loop operating mode, and the like).

The web-based tool presents the end user with a variety of interactive web pages that include graphical elements, menus, text entry fields, search fields, output/results screens, and the like. For example, the web-based tool may include the following functionality, without limitation: a search page that allows the user to select or identify healthcare professionals or groups for purposes of comparing patient data; geographical map displays that identify patient locations in connection with designated treatment and/or demographic criteria; output pages or displays that allow users to review the clinical outcomes of their own patients, with or without a comparison to the clinical outcomes of other patients; economic summary pages or displays that identify areas where the user or the user's patients can reduce healthcare costs associated with the treatment provided by the user; and recommendation pages or displays that provide tips, guidance, and suggestions to improve the treatment plan, therapy, and medical outcome of the patient. These and other features and functions enable a healthcare professional to quickly and easily review results that are based on an analysis of relevant patient data gathered for a large population of patients, wherein those results can have a positive impact on at least some of the patients under the care of that healthcare professional.

For the sake of brevity, conventional features and functionality related to infusion systems, insulin pumps, infusion sets, and fluid reservoirs may not be described in detail here. Examples of infusion pumps and/or related pump drive systems used to administer insulin and other medications may be of the type described in, but not limited to, U.S. Pat. Nos. 5,505,709; 6,485,465; 6,554,798; 6,558,351; 6,659,980; 6,752,787; 6,817,990; 6,932,584; and 7,621,893; which are herein incorporated by reference.

As used herein, an "outcome" is a patient-related result having some correlation to medical treatment or therapy. For the exemplary embodiment described herein, a "glycemic outcome" is a patient-related result that is associated with the patient's glycemic state, diabetes therapy, insulin status, condition of the insulin infusion device, or the like. More specifically, a glycemic outcome can correspond to a status of blood sugar levels, such as high, low, variable, in range, etc., and/or to a test score or value that is indicative of glycemic health (such as the commonly used A1C value).

As used herein, a "glycemic insight" is a statistically derived association between an action/event (or a collection of actions/events) and a corresponding glycemic outcome as measured by glucose readings.

Turning now to the drawings, FIG. 1 is a simplified block diagram representation of an operating environment 100 that is suitably configured to support the techniques and methodologies described in more detail below. The operating environment 100 supports users of insulin infusion devices, and supports various techniques and methods to help end users (patients, caregivers, healthcare providers, parents, etc.) manage the use of insulin infusion devices. It should be appreciated that FIG. 1 depicts one possible implementation of the operating environment 100, and that other arrangements, architectures, and deployments can be provided if so desired. The operating environment 100 (which has been simplified for purposes of illustration) generally includes or cooperates with the following components, without limitation: a cloud-based patient therapy management system 102; a user device 104; and a database system 106 associated with the patient therapy management system 102. The operating environment 100 may also include or support at least one medical device 108 (owned, operated, or otherwise used by a patient), and at least one presentation device 110 (owned, operated, or otherwise used by the patient).

The management system 102 and the user device 104 are communicatively coupled to a data communication network (not shown). In certain embodiments, the user device 104 communicates with the medical device 108, directly or via a data communication network, and/or communicates with the presentation device 110, directly or via a data communication network. In practice, the operating environment 100 may cooperate with and leverage any number of wireless and any number of wired data communication networks maintained or operated by various entities and providers. Accordingly, communication between the various components shown in FIG. 1 may involve multiple network links and different data communication protocols. In this regard, a network utilized in the operating environment 100 can include or cooperate with any of the following, without limitation: a local area network; a wide area network; the Internet; a personal area network; a cellular communication network; a satellite communication network; a video services or television broadcasting network; a network onboard a vehicle; or the like. To this end, hardware components in the operating environment 100 may be suitably configured to support a variety of wireless and wired data communication protocols, technologies, and techniques as needed for compatibility with the network infrastructure.

In accordance with certain exemplary embodiments, the patient therapy management system 102 is implemented as at least one computer-based or processor-based component. For simplicity and ease of illustration, FIG. 1 depicts the system 102 as a single block—it should be appreciated that any number of distinct hardware components can be utilized to implement the system 102. An exemplary embodiment of a device suitable for implementing the system 102 is described below with reference to FIG. 2.

The patient therapy management system 102 can be considered the "heart" of the operating environment 100. The system 102 includes or cooperates with the database system 106 (which is realized using one or more components) to support the functionality and operation described in more detail below. The system 102 collects and analyzes patient data 112 for a plurality of different patients, typically a very large population of patients under the care of many different caregivers. The database system 106 collects, stores, and maintains the patient data for the population of patients. In this regard, FIG. 1 depicts patient data 112a associated with Patient 1, patient data 112b associated with Patient 2, and so on, including patient data 112n associated with Patient N, where N can be any number of different patients. The patient data for any one patient can originate from various sources, including, without limitation: an insulin infusion device; a continuous glucose sensor; a blood glucose meter; a smartphone or other type of personal mobile device; a computing device; an activity tracker; a meal logging device or application; a mood tracking device or application; a GPS device; a vehicle owned or operated by the patient; a wearable smart device; a smart home controller system; a video game system; home entertainment equipment; etc. The system 102 can receive any or all of the patient data directly from one or more of these data sources. Alternatively or additionally, the system 102 can receive any or all of the patient data indirectly by way of a suitably configured data uploader component (not shown), which in turn receives the patient data from one or more of the originating sources.

The user device 104 is a client device that is owned or operated by the user, e.g., a caregiver, a healthcare provider, a nurse, a payor, a doctor, a patient, or the like. In certain embodiments, some or all of the functionality and processing intelligence of the patient therapy management system 102 can reside at the user device 104. In other words, the operating environment 100 need not rely on a network-based or a cloud-based server arrangement, although such a deployment might be the most efficient and economical implementation. In other embodiments, some or all of the functionality and processing intelligence of the system 102 can reside at the medical device 108, the presentation device 110, and/or at other compatible components or computing devices. These and other alternative arrangements are contemplated by this disclosure. To this end, some embodiments of the operating environment 100 may include additional devices and components that serve as data sources, data processing units, and/or content delivery mechanisms. For example, the operating environment 100 may include any or all of the following elements, without limitation: computer devices or systems; patient monitors; healthcare provider systems; data communication devices; and the like.

The user device 104 can be realized using a variety of different device platforms. For example, the user device 104 can be implemented as any of the following, without limitation: a cellular telephone or smartphone; a portable computer (e.g., a laptop, a tablet, or a netbook computer); a portable media player; a portable video game device; a portable medical device; a navigation device such as a global positioning system (GPS) device; a wearable computing device; an electronic toy or game; etc. In accordance with certain exemplary embodiments, each user device 104 supported by the system 102 is implemented as a computer-based or processor-based component. For simplicity and ease of illustration, FIG. 1 depicts only one user device 104. In practice, however, the system 102 is suitably configured to support a plurality of user devices 104 (for example, to support a plurality of different caregivers). An exemplary embodiment of a device suitable for implementing the user device 104 is described below with reference to FIG. 2.

The remainder of this description assumes that the user device 104 is a computer device (a desktop computer, a laptop computer, a tablet device, a mobile device, etc.) used by the particular end user. To this end, the configuration and general functionality of the user device 104 can be substantially consistent with conventional personal computer design. In this regard, a web browser application 120 is installed on the user device 104 to allow the end user to access and utilize a suitably configured and designed therapy management website that is maintained and provided by the patient therapy management system 102. The therapy management website allows the end user to organize and view patient data, obtain therapy recommendations based on patient data, and receive content related to patient therapy (e.g., messages, notifications, recommendations, instructions, and guidance) as generated by the system 102. In certain embodiments, the web browser application 120 and the associated therapy management website can be manipulated to upload patient data to the system 102 for storage and analysis.

The medical device 108 is used by the patient who is under observation by the end user (the operator of the user device 104). In a typical scenario, the end user is a doctor and the medical device 108 is an insulin infusion device, an infusion set, or a continuous glucose sensor used by the doctor's patient. Although not always required or needed, the user device 104 can communicate with the medical device 108 to provide therapy related content (messages, reminders, recommended adjustments for the medical device 108, alerts, or the like) and/or commands or instructions that can be executed by the medical device to automatically adjust certain device settings, control the therapy (e.g., control the delivery of insulin by an infusion pump), or otherwise remotely control or influence the operation of the medical device.

For simplicity and ease of illustration, FIG. 1 depicts only one medical device 108. In practice, however, the system 102 is suitably configured to support a plurality of medical devices per patient. An exemplary embodiment of a device suitable for implementing the medical device 108 is described below with reference to FIG. 2.

The presentation device 110 is a client device that is owned or operated by the patient. In certain embodiments, some or all of the functionality and processing intelligence of the patient therapy management system 102 can reside at the presentation device 110. The presentation device 110 can be realized using a variety of different device platforms, including any of the platforms listed above for the user device 104. In accordance with certain exemplary embodiments, each presentation device 110 is implemented as a computer-based or processor-based component. For simplicity and ease of illustration, FIG. 1 depicts only one presentation device 110. In practice, however, any number of distinct presentation devices 110 can be in data communication with the user device 104 and/or the system 102. An exemplary embodiment of a device suitable for implementing the presentation device 110 is described below with reference to FIG. 2.

The remainder of this description assumes that the presentation device 110 is a computer device (a desktop computer, a laptop computer, a tablet device, a mobile device, etc.) used by the particular patient. To this end, the configuration and general functionality of the presentation device 110 can be substantially consistent with conventional personal computer design. In this regard, a web browser application 130 (or a suitably configured and compatible application) is installed on the presentation device 110 to allow the patient to access and utilize a suitably configured and designed patient portal website that is maintained and provided by the patient therapy management system 102. The patient portal website allows the patient to organize and view patient data, obtain therapy recommendations based on patient data, and receive content related to patient therapy (e.g., messages, notifications, recommendations, instructions, and guidance) as generated by the system 102. In certain embodiments, the web browser application 130 and the associated therapy management website can be manipulated to upload individual patient data to the system 102 for storage and analysis.

Figure 2:
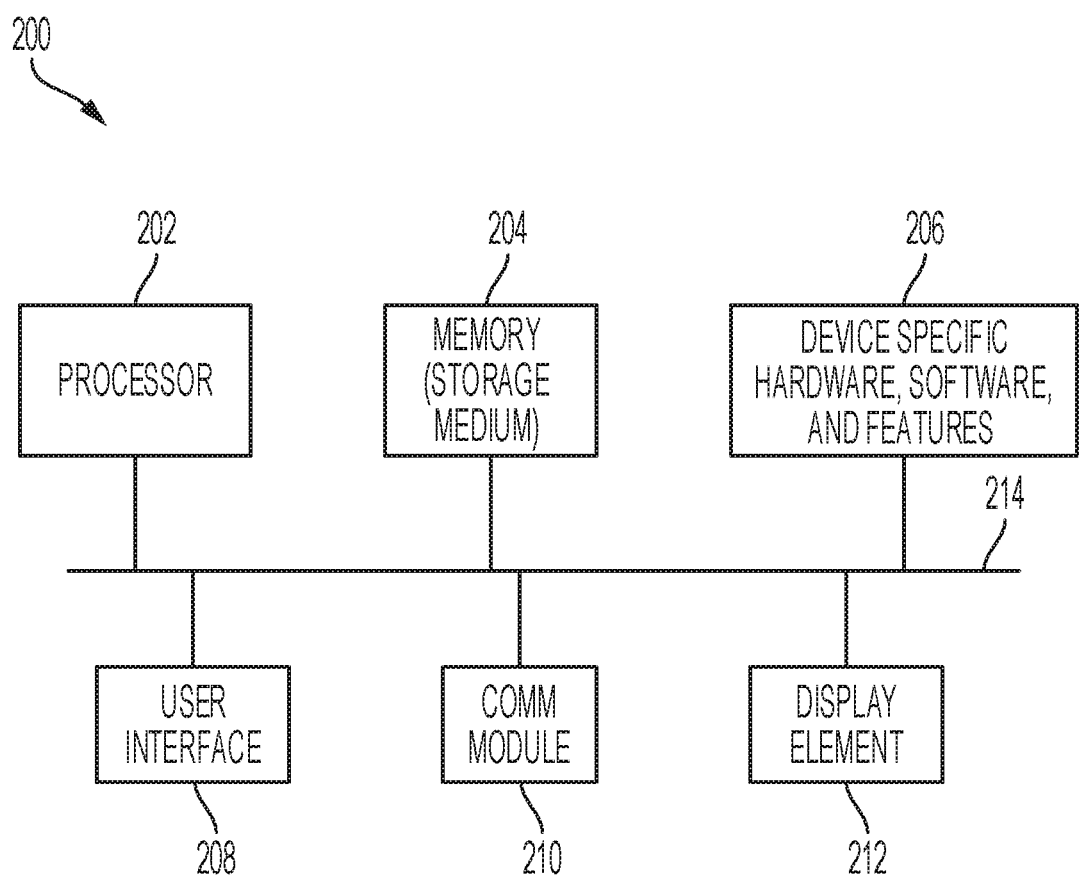
FIG. 2 is a simplified block diagram representation of an exemplary embodiment of a computer-based or processor-based device suitable for deployment in the operating environment shown in FIG. 1.

As mentioned above, the operating environment 100 includes or cooperates with computer-based and/or processor-based components having suitably configured hardware and software written to perform the functions and methods needed to support the features described herein. For example, the patient therapy management system 102, each user device 104, the medical device 108, and the presentation device 110 can be realized as an electronic processor-based component. In this regard, FIG. 2 is a simplified block diagram representation of an exemplary embodiment of a computer-based or processor-based device 200 that is suitable for deployment in the system shown in FIG. 1.

The illustrated embodiment of the device 200 is intended to be a high-level and generic representation of one suitable platform. In this regard, any of the computer-based or processor-based components mentioned here can utilize the architecture of the device 200. The illustrated embodiment of the device 200 generally includes, without limitation: at least one processor 202; a suitable amount of memory 204; device-specific hardware, software, firmware, and/or features 206; a user interface 208; a communication module 210; and a display element 212. Of course, an implementation of the device 200 may include additional elements, components, modules, and functionality configured to support various features that are unrelated to the subject matter described here. For example, the device 200 may include certain features and elements to support conventional functions that might be related to the particular implementation and deployment of the device 200. In practice, the elements of the device 200 may be coupled together via a bus or any suitable interconnection architecture 214.

The processor 202 may be implemented or performed with a general purpose processor, a content addressable memory, a digital signal processor, an application specific integrated circuit, a field programmable gate array, any suitable programmable logic device, discrete gate or transistor logic, discrete hardware components, or any combination designed to perform the functions described here. Moreover, the processor 202 may be implemented as a combination of computing devices, e.g., a combination of a digital signal processor and a microprocessor, a plurality of microprocessors, one or more microprocessors in conjunction with a digital signal processor core, or any other such configuration.

The memory 204 may be realized as RAM memory, flash memory, EPROM memory, EEPROM memory, registers, a hard disk, a removable disk, a CD-ROM, or any other form of storage medium known in the art. In this regard, the memory 204 can be coupled to the processor 202 such that the processor 202 can read information from, and write information to, the memory 204. In the alternative, the memory 204 may be integral to the processor 202. As an example, the processor 202 and the memory 204 may reside in an ASIC. At least a portion of the memory 204 can be realized as a computer storage medium, e.g., a tangible computer-readable medium having computer-executable instructions stored thereon. The computer-executable instructions, when read and executed by the processor 202, cause the device 200 to perform certain tasks, operations, functions, and processes that are specific to the particular embodiment. In this regard, the memory 204 may represent one suitable implementation of such computer-readable media. Alternatively or additionally, the device 200 could receive and cooperate with computer-readable media (not separately shown) that is realized as a portable or mobile component or platform, e.g., a portable hard drive, a USB flash drive, an optical disc, or the like.

The device-specific hardware, software, firmware, and features 206 may vary from one embodiment of the device 200 to another. For example, the device-specific hardware, software, firmware, and features 206 will support: smartphone functions and features when the device 200 is realized as a mobile telephone; conventional personal computer functions and features if the device 200 is realized as a laptop or tablet computer; insulin pump operations when the device 200 is realized as an insulin infusion device; etc. In practice, certain portions or aspects of the device-specific hardware, software, firmware, and features 206 may be implemented in one or more of the other blocks depicted in FIG. 2.

The user interface 208 may include or cooperate with various features to allow a user to interact with the device 200. Accordingly, the user interface 208 may include various human-to-machine interfaces, e.g., a keypad, keys, a keyboard, buttons, switches, knobs, a touchpad, a joystick, a pointing device, a virtual writing tablet, a touch screen, a microphone, or any device, component, or function that enables the user to select options, input information, or otherwise control the operation of the device 200. The user interface 208 may include one or more graphical user interface (GUI) control elements that enable a user to manipulate or otherwise interact with an application via the display element 212.

The communication module 210 facilitates data communication between the device 200 and other components as needed during the operation of the device 200. In the context of this description, the communication module 210 can be employed to transmit or stream device-related control data, patient data, device-related status or operational data, messages and notifications, therapy related content, and the like. It should be appreciated that the particular configuration and functionality of the communication module 210 can vary depending on the hardware platform and specific implementation of the device 200. In practice, an embodiment of the device 200 may support wireless data communication and/or wired data communication, using various data communication protocols. For example, the communication module 210 could support one or more wireless data communication protocols, techniques, or methodologies, including, without limitation: RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB. Moreover, the communication module 210 could support one or more wired/cabled data communication protocols, including, without limitation: Ethernet; powerline; home network communication protocols; USB; IEEE 1394 (Firewire); hospital network communication protocols; and proprietary data communication protocols.

The display element 212 is suitably configured to enable the device 200 to render and display various screens, recommendation messages, notifications, GUIs, GUI control elements, drop down menus, auto-fill fields, text entry fields, message fields, or the like. Of course, the display element 212 may also be utilized for the display of other information during the operation of the device 200, as is well understood. Notably, the specific configuration, operating characteristics, size, resolution, and functionality of the display element 212 can vary depending upon the practical implementation of the device 200. For example, if the device 200 is a laptop computer, then the display element 212 may be a relatively large monitor. Alternatively, if the device 200 is a cellular telephone device, then the display element 212 may be a relatively small integrated display screen, such as a touch-sensitive screen.

Figure 3:
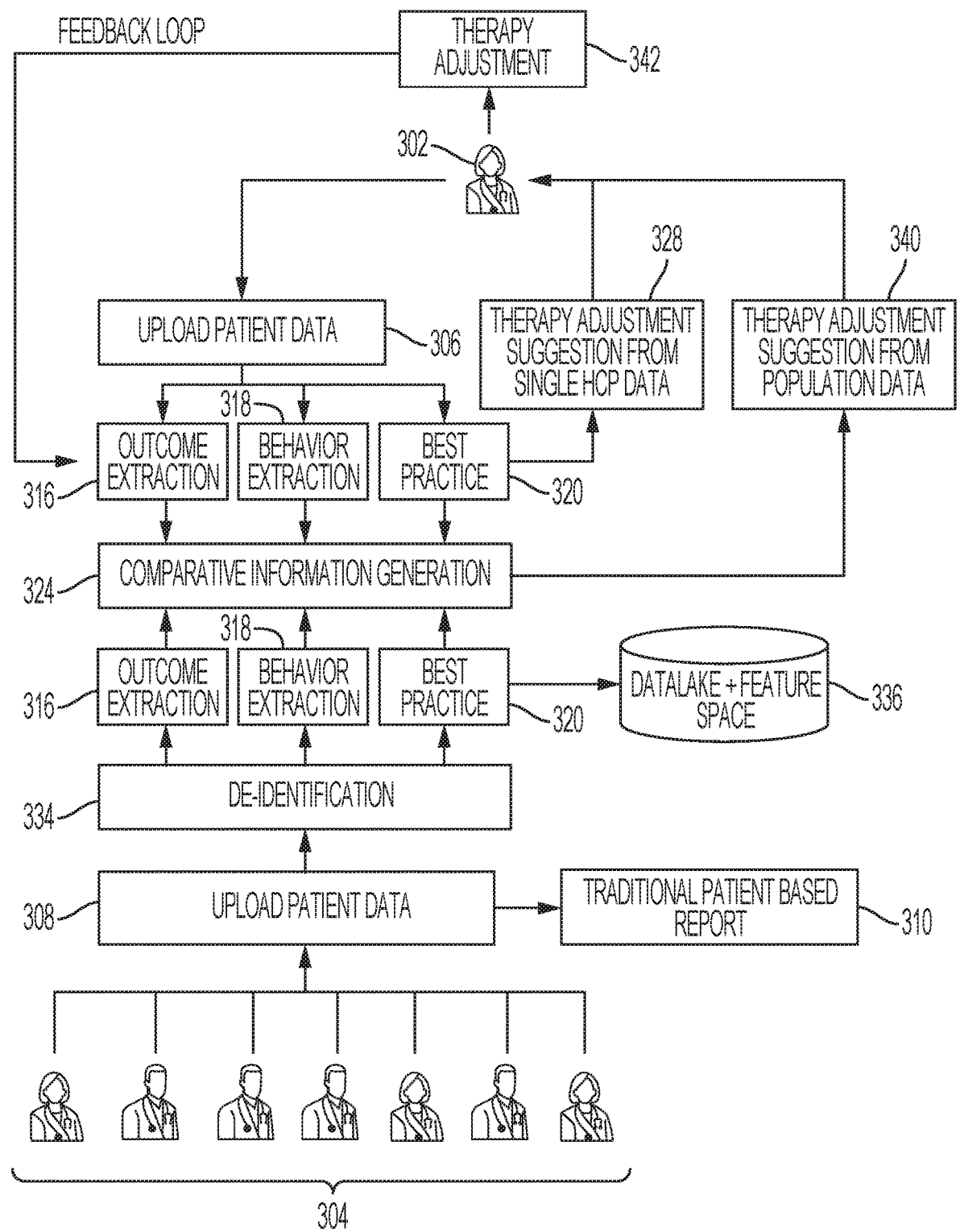
FIG. 3 is a diagram that illustrates a typical use case that can be supported by the patient therapy management system shown in FIG. 1.

FIG. 3 is a diagram that illustrates a typical use case that can be supported by the system shown in FIG. 1. For the illustrated example, a plurality of different healthcare professionals (HCPs) upload patient data corresponding to their respective patients. FIG. 3 depicts a customer HCP 302 and a plurality of contributing HCPs 304. The customer HCP 302 represents the user of the system for this use case. The customer HCP 302 uploads patient data (task 306) for those patients under the care of the customer HCP 302. Similarly, each of the contributing HCPs 304 uploads patient data (task 308) for those patients under their own care. The uploaded patient data received from the contributing HCPs 304 can be analyzed, processed, and otherwise utilized to generate traditional patient based reports 310 if so desired. Although not shown in FIG. 3, the uploaded patient data received from the customer HCP 302 can also be analyzed, processed, and otherwise utilized to generate traditional patient based reports 310.

The uploaded patient data received from the customer HCP 302 is subjected to various routines, procedures, algorithms, and/or processes to obtain useful and insightful information related to the management of patient therapy. In accordance with the illustrated embodiment, the uploaded patient data is subjected to an outcome extraction process 316, a behavior extraction process 318, and a best practice process 320. The outcome extraction process 316 handles glycemic related insights such as percent of time in desired glucose range, number of low and high glycemic excursions, A1C score, or the like. The results can include when the patient enables an automated insulin delivery mode, when the patient spends more time in euglycemic range, and the like. The behavior extraction process 318 extracts insights related to patient behavior after an event which impacts the patient's glucose levels. These events can include meals (based on the content of carbohydrate, fat, and protein), exercise (based on the intensity and duration), bolus doses, or the like. The generated insights can indicate, for example, that if the patient takes an insulin dose of 5 units and exercises for 30 minutes, the patient will most likely have a low excursion within 2 hours. The best practices process 320 identifies those actions taken by the patient which resulted in optimal outcomes. These insights can include, for example, the combination of carbohydrate content, exercise duration, and exercise intensity the patient follows to maintain good glycemic outcomes.

The output or results of the processes 316, 318, 320 may be utilized in connection with a comparative information generation process 324. In addition, the output or results of the best practice process 320 can be used to generate and provide a therapy adjustment suggestion (task 328). In this regard, based on the analysis performed at the outcome extraction, behavior extraction, and best practice modules, the insights generated will help understand the optimal therapy required to drive best outcomes and identify therapy practices that lead to poor outcomes. Hence, therapy recommendations can be provided to further improve the outcomes. The HCP is notified regarding which practices lead to good outcomes and which practices can be further improved. Notably, task 328 relies on patient data provided by only one HCP, namely, the customer HCP 302. The therapy adjustment suggestion generated at task 328 is communicated to the customer HCP 302 using, for example, the web-based tool described above.

The uploaded patient data received from the contributing HCPs 304 is subjected to de-identification (task 334) to protect the patients' health information (the patients cannot be identified or re-identified in the future). Specific identifiers such as name, email addresses, phone number, and social security numbers are removed. Moreover, statistical methods can be used to alter or encrypt sensitive or protectable data. Thereafter, the patient data is subjected to the outcome extraction process 316, the behavior extraction process 318, and the best practice process 320, which were described above. As mentioned above, the output or results of the processes 316, 318, 320 (as applied to the patient data obtained from the contributing HCPs) may be utilized in connection with the comparative information generation process 324. In addition, the output or results of the best practice process 320 can be provided to a data lake and feature space database 336. The data lake and feature space stores all the insights at the personalized and population level. As more patient data gets uploaded in the system, the personal and population level insights need to be evaluated and updated accordingly. The insights will be flagged by the relevant features to speed up the feature retrieval for the comparative information generation module.

The comparative information generation process 324 identifies and analyzes patient data from the contributing HCPs 304 that satisfies certain criteria, identifies and analyzes patient data from the customer HCP 302 that satisfies certain criteria, and generates comparative output that may be realized as: reports, recommendations, alerts, suggestions, graphical representations of patient data, control or command instructions for a medical device, or the like. The criteria that governs the comparative analysis is dictated by the type of report or information requested by the customer HCP 302. To this end, some of the criteria can be designated by the customer HCP 302, and other criteria may be predefined or designated by default based on the type of information that is requested by the customer HCP 302, based on the format of the desired output, or the like.

The comparative information generation process 324 allows the customer HCP 302 to compare therapy or treatment related information for his/her patient (or group of patients) against the corresponding information for a population of other patients. Moreover, the process 324 allows the customer HCP 302 to specify patient attributes or criteria to define the population of other patients that will be utilized to formulate the comparison. The output or results of the comparative information generation process 324 can be used to generate and provide a therapy adjustment suggestion (task 340). Notably, task 340 relies on patient data provided by a plurality of different HCPs, namely, the contributing HCPs 304. The therapy adjustment suggestion generated at task 340 is communicated to the customer HCP 302 using, for example, the web-based tool described above. Based on retrospective analysis of the patient data, the system will provide therapy recommendations to the HCP. The HCP has the discretion to accept or decline these therapy recommendations based on the HCP's expertise. The HCP can also partially accept the therapy recommendation. Moreover, the therapy change recommendations provided by the HCP in response to the reports are collected for analysis to detect therapy changes compared to earlier patient therapy/behavior.

The customer HCP 302 can view and/or interact with the therapy adjustment suggestion(s) as needed. In certain embodiments, a therapy adjustment suggestion includes an active control element to enable the customer HCP 302 to initiate an automated therapy adjustment (task 342) at the patient's medical device. Alternatively or additionally, the customer HCP 302 can adjust the medical device for the patient or provide appropriate instructions to the patient.

Feedback on the actual recommendation provided by the HCP is collected and provided for incorporation into and consideration by the outcome extraction, behavior extraction, and best practice modules. The arrowhead at the end of the illustrated feedback loop indicates that the feedback data is provided to all three of these blocks. The feedback information helps to fine tune future therapy recommendations as well as to correct or improve previous recommendations.

The patient therapy management system 102 collects and analyzes a large amount of patient data in an aggregated manner, which enables it to generate therapy related information that benefits other patients (i.e., patients that did not contribute data to the aggregated set of patient data). The aggregated patient data can be processed and analyzed using, for example: machine learning algorithm(s); expert system technology; artificial intelligence techniques; a knowledge base; natural language processing; and/or similar methodologies. The system 102 provides an interactive way for an HCP to leverage aggregated patient data for a large population of patients under the care of different HCPs, in a way that benefits an individual patient or a distinct group of patients that are outside of the analyzed population. The output generated by the system 102 enables HCPs to make immediate therapy related decisions based on information collected for a large population of patients, rather than relying only on the history of each individual patient. The system 102 analyzes aggregated patient data for a first group of patients (being managed by any number of different HCPs) to generate useful output (graphs, charts, reports, notifications, statistics related to patient behavior, statistics related to medical device usage or performance, statistics related to medical device alarms or alerts, and so on) that are intended to benefit an individual patient who is not a member of the first group of patients and/or a second group of patients that differs from the first group of patients. In preferred implementations, the system 102 generates, maintains, and updates a web portal to provide the useful therapy related output to end users, namely, HCPs. An end user can conveniently log into the web portal using his or her credentials to access the various features and functionality described here. In practice, the web portal can be accessed using any device that is web-enabled, browser-based, HTTP compatible, or the like.

A doctor using the patient therapy management system 102 can quickly and conveniently determine whether or not treatment of his or her patients resulted in better or worse outcomes, relative to a defined population of patients treated by other doctors. The comparison of a customer HCP's patient or patient population against a different patient population can inform the customer HCP in a way that allows the customer HCP to modify therapy or treatment plans going forward to better serve the customer HCP's patients.

Accordingly, the system 102 provides useful information and messages to HCPs so that the HCPs can understand how to obtain better patient outcomes based on a large aggregated amount of "third party" patient data. Many processes and behaviors result in fluctuations in blood glucose levels. Commonly recognized processes impacting blood glucose levels include food, exercise, disease (acute or chronic), medication (insulin, oral, and other types), stress and sleep patterns, and the like. Furthermore, behavioral factors such as the time of the day, attentiveness to therapy, and the proper use and maintenance of the insulin infusion system can provide additional quantitative indications of the underlying factors impacting glucose control. These and other aspects of patient care can be monitored and modified in an efficient and effective manner with the system 102.

In practice, the system 102 requires a minimum amount of input data per patient before it can generate intelligent and accurate results. For example, it may be necessary to collect patient data for at least one full day. Going forward, however, the information output by the system 102 will progressively become more sophisticated and accurate as more and more patient data is collected and analyzed. In this regard, the techniques and methodologies described herein assume that the sources of input data (such as glucose sensors, blood glucose meters, physiological sensors, and the like) are each operating within an acceptable range of accuracy.

In certain embodiments, the system 102 obtains some patient data in the form of mobile device data provided by the patient's mobile device. The mobile device data can include any type of data or information generated by the mobile device, forwarded by the mobile device, entered at the mobile device, detected by the mobile device, or the like. For example, and without limitation, the mobile device data can include time stamp data, calendar data, mobile app data, status information related to the operation of the mobile device, and/or sensor data generated by sensors or detectors onboard the mobile device (such as an accelerometer, a gyroscope, a light sensor, a camera, a thermometer, a biometric scanner, etc.).

Data Inputs

There are many factors that can influence a patient's blood glucose levels. Various factors may also influence how best to control and manage the patient's blood glucose. The glycemic insights methodology presented here is based on the collection and analysis of data, which need not be specifically related to blood glucose (BG) meter measurements, glucose sensor readings, or insulin delivery information. Although the system 102 obtains and analyzes such data, it may also obtain and consider additional data. The system 102 may also process data received directly or indirectly from other physiological sensors, devices, or equipment. For example, an embodiment of the system 102 can be suitably configured to analyze respiratory data, electrocardiogram data, body temperature data, heartrate information, and the like.

The system 102 is suitably configured to receive and process a variety of input data from multiple sources. Moreover, the system 102 is designed to be flexible and scalable to accommodate additional input data types as needed. The number of input data sources and the amount of input data handled by the system 102 may vary from one embodiment to another, depending on the particular implementation and intended application. In accordance with the embodiment described here, some or all of the following input data can be used for purposes of generating output intended for HCPs. The following summary of specific input data types is not intended to be exhaustive or otherwise limiting, and alternative or additional input data can be considered in an embodiment of the system 102.

Carbohydrate amount—this refers to the carbohydrate amount that one Unit of insulin can compensate to maintain the current glucose level. The carbohydrate amount is usually expressed in grams or milligrams. The patient's mobile device will usually be the source of this data.

Bolus information—the bolus information includes the bolus dosage amount (in Units of insulin), the date/time of delivery (time of day and calendar data), and the bolus type (normal, square, or dual). The insulin infusion device will usually be the source of this data.

Insulin to carbohydrate ratio—this is a patient-specific parameter that relates to how much insulin the patient needs to compensate for a designated unit (e.g., one gram) of carbohydrate. The insulin to carbohydrate ratio is expressed in grams/Unit. The insulin infusion device will usually be the source of this data.

Insulin sensitivity factor—this is a patient-specific parameter that relates to the reduction in blood glucose in response to one Unit of insulin. The particular manner in which the insulin sensitivity factor is calculated is determined by the specific pumping protocol. The insulin sensitivity factor is expressed in mg/dL/U (milligrams per deciliter per Unit). The insulin infusion device will usually be the source of this data.

Active insulin amount—this refers to how much insulin is still active in the body of the patient from previous bolus doses. This quantity is expressed in Units of insulin. The insulin infusion device will usually be the source of this data.

Time of day—this refers to timestamp and/or date stamp information, which may be associated with or appended to any other piece of input data to provide a time reference.

Basal rate—this is a patient-specific parameter that indicates the basal rate of insulin delivery, which is usually expressed in Units/hour. The insulin infusion device will usually be the source of this data.

Temporary basal use—this refers to an occurrence during which the patient temporarily "overrides" the nominal or usual basal rate of insulin. The system employs a Boolean value that indicates the activation of the temporary basal mode, and also indicates the temporary basal rate value. The insulin infusion device will usually be the source of this data.

Consecutive boluses—this refers to an occurrence of back-to-back insulin boluses, which are delivered within a designated period of time. The system employs a Boolean value that indicates the occurrence of consecutive boluses, and also indicates the total volume of the boluses delivered during the designated period of time. The insulin infusion device will usually be the source of this data.

Insulin suspension—this refers to a period of time during which the insulin infusion device has been temporarily suspended (insulin delivery is temporarily halted). The data related to insulin suspension can include some or all of the following, without limitation: threshold setting; suspension duration; active insulin before the suspension; sensor rate of change around the suspension; carbohydrate intake around the suspension; time (day of week, time of day) of the suspension; how the suspension recovered; and user response to the suspension. The insulin infusion device will usually be the source of this data.

Reservoir rewind and priming time—this refers to activities associated with the installation of a new insulin reservoir into the insulin infusion device. This requires a rewind action to retract the reservoir actuator, which facilitates removal of the used reservoir. After installing the new reservoir, the fluid flow path is primed for insulin delivery. The insulin infusion device will usually be the source of this data.

Pump alarms and associated alarm times—pump alarms can be generated by the insulin infusion device for various reasons. Pump alarm data indicates the type of alarm and the corresponding alarm time. The insulin infusion device will usually be the source of this data.

Sensor alerts and alert times—sensor alerts can be generated by the insulin infusion device and/or the glucose sensor for various reasons. Sensor alert data indicates the type of sensor alert and the corresponding alert time. The insulin infusion device and/or the glucose sensor can be the source of this data.

Blood glucose readings and measurement times—blood glucose readings are usually expressed in mg/dl, and are obtained from a blood glucose meter. The insulin infusion device, the blood glucose meter, or the patient's mobile device can be the source of this data.

User demographic information—this data may include, without limitation, the patient's age, number of years using insulin, medical diagnosis, age at the onset of diabetes, sex, medication types, and the like. User demographic information can be provided by the patient's mobile device, the insulin infusion device, a webpage user interface, or the like.

Meal time and content—this data relates to the timing of meal consumption and the type and amount of food consumed. The patient's mobile device will usually be the source of this data. In this regard, a suitably configured mobile app can include a feature or functionality that allows the patient to specify meal times and to estimate the type and amount of food consumed at each meal. In certain scenarios, this data can be imported from a third party (partner) database directly, rather than having patients redundantly enter the information into the mobile app.

Exercise time and content—this data relates to the timing of exercise and the type, duration, and amount of exercise performed by the patient. The patient's mobile device or an activity tracker device will usually be the source of this data. In this regard, a suitably configured mobile app can include a feature or functionality that allows the patient to specify exercise times and to estimate the type and amount of exercise. In certain scenarios, this data can be imported from a third party (partner) database directly, rather than having patients redundantly enter the information into the mobile app.

Medication type, dosage, and time—this data relates to instances when the patient takes medication (other than insulin), and the data indicates the type of medication, the dosage taken, and the time that the medication was taken. The patient's mobile device will usually be the source of this data. In some scenarios, a smart insulin pen or other type of smart insulin delivery device can be the source of this data. In this regard, a suitably configured mobile app can include a feature or functionality that allows the patient to record information associated with taking medication.

Sleep time and quality—this data indicates sleeping periods, and information related to the quality or type of sleep experienced by the patient. The sleep-related information can be provided by a patient monitor (activity tracker) or, in certain embodiments, the sleep-related information is provided by a suitably configured mobile app running on the patient's mobile device. In such an embodiment, the mobile app allows the patient to enter the relevant sleep-related information. In accordance with some embodiments, sleep related information can be calculated using accelerometer data, heartrate data, ambient lighting measurements, glucose levels, etc.

Stress time—this data indicates periods of stress experienced by the patient. The stress-related information can be derived from physiological factors and/or measurable data such as heart rate, blood pressure, skin conductance, body temperature, or the like. Additionally or alternatively, the stress-related information can be based on user input. Accordingly, the patient's mobile device can be the source of this data. A suitably configured mobile app can include a feature or functionality that allows the patient to record information associated with periods of stress.

Electronic medical records and lab test data—this data can be provided by healthcare providers, medical facilities, insurance companies, or the like. In certain scenarios, this data can be imported from a third party (partner) database directly, rather than having patients redundantly enter the information into the mobile app.

Figure 4:
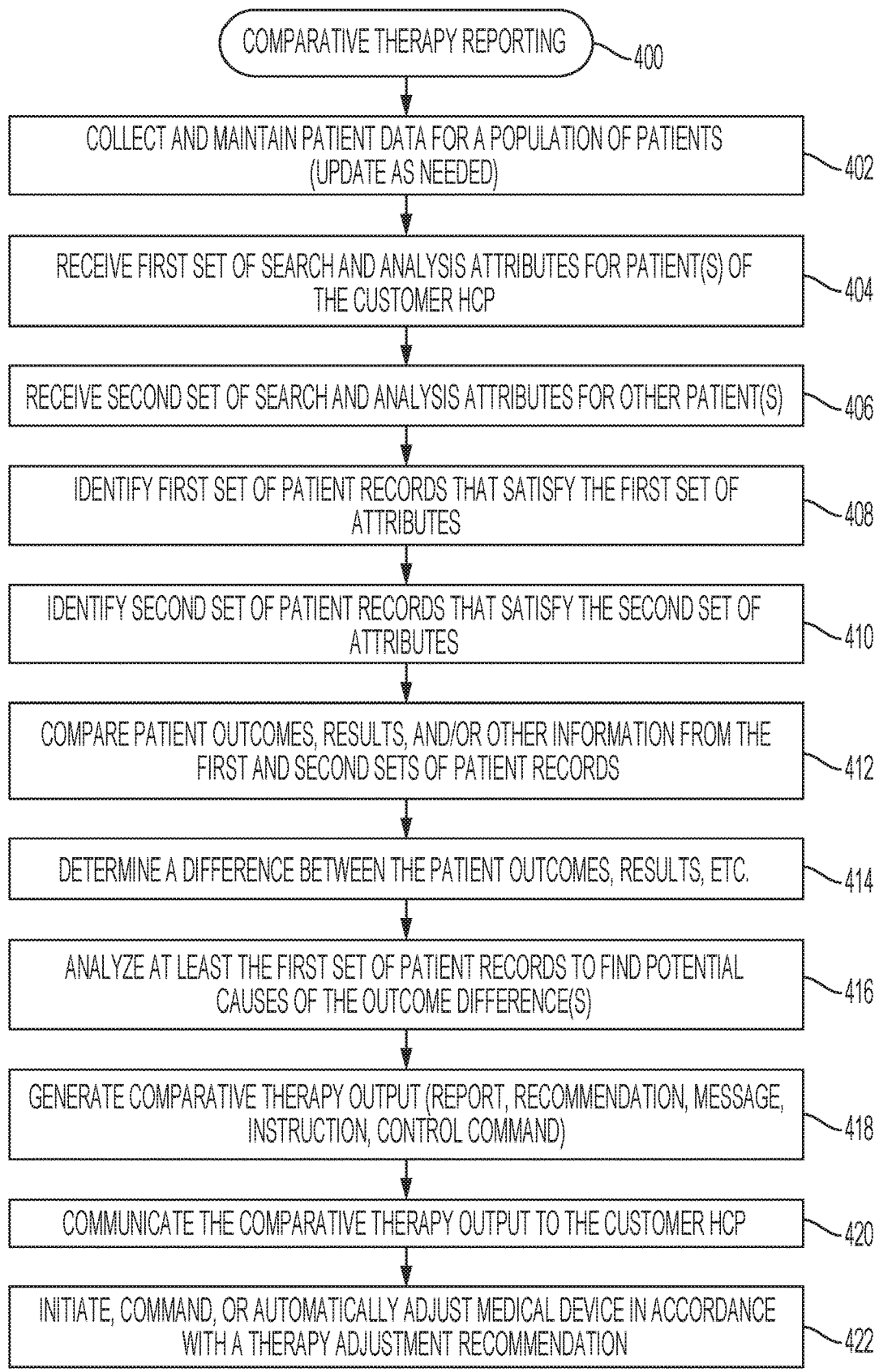
FIG. 4 is a flow chart that illustrates an exemplary embodiment of a comparative therapy reporting process.

FIG. 4 is a flow chart that illustrates an exemplary embodiment of a comparative therapy reporting process 400. The process 400 represents one suitable implementation of a method of generating and communicating comparative therapy information for medical device users. The various tasks performed in connection with the process 400 may be performed by software, hardware, firmware, or any combination thereof. For illustrative purposes, the following description of the process 400 may refer to elements mentioned above in connection with FIGS. 1-3. It should be appreciated that the process 400 may include any number of additional or alternative tasks, the tasks shown in FIG. 4 need not be performed in the illustrated order, and the process 400 may be incorporated into a more comprehensive procedure or process having additional functionality not described in detail herein. Moreover, one or more of the tasks shown in FIG. 4 could be omitted from an embodiment of the process 400 as long as the intended overall functionality remains intact.

The process 400 utilizes patient data that is associated with a population of different patients, which in turn are under the care of different HCPs. To this end, at task 402 the process 400 collects patient data that is associated with a plurality of medical device users (patients), such as diabetic patients that use insulin infusion pumps. Treatment of these patients is managed by a plurality of different HCPs, including a customer HCP and other non-customer HCPs. In this context, the customer HCP represents an intended end user of the system, and the intended recipient of the output that results from the process 400. In contrast, the non-customer HCPs are considered to be "contributors" relative to the customer HCP in that the patient data associated with non-customer HCPs is leveraged for the benefit of the customer HCP.

The patient data can be obtained from the patients, from the HCPs, directly from medical devices or other devices owned or operated by the patients/HCPs, indirectly via a data uploader device or system, or the like. The patient data can be obtained and updated in an ongoing manner, e.g., periodic data uploads, near real-time data transfer, manual data uploads, or the like. In accordance with the exemplary use case presented here, where the medical device users are insulin infusion device users, the patient data for any individual patient may include any or all of the following, without limitation: carbohydrate amount; bolus information; insulin to carbohydrate ratio; insulin sensitivity factor; active insulin amount; time of day; basal rate; temporary basal use; consecutive boluses; insulin suspension; reservoir rewind time; reservoir priming time; pump alarms and associated alarm times; sensor alerts and associated alert times; blood glucose readings and associated measurement times; user demographic information; meal times and corresponding meal content; exercise times and corresponding exercise content or type; medication type, dosage, and time; sleep time and quality; stress time; and electronic medical records; medical lab test data. Of course, the specific type and amount of data collected for each patient can vary from one implementation to another, depending on patient characteristics, medical device characteristics, the condition(s) being treated, HCP preferences, and other practical factors.

In accordance with the exemplary embodiment presented here, the customer HCP can define, select, or otherwise designate patient attributes to be used for purposes of searching and analysis of patient data. The patient attributes define the groups of patients to be compared. More specifically, the customer HCP can identify certain patient attributes for one or more patients under the care of the customer HCP. Likewise (although not always required), the customer HCP can identify certain patient attributes for one or more other patients, e.g., patients under the care of one or more non-customer HCPs. In some scenarios, the other patients can include patients under the care of the same customer HCP (for example, a doctor may want to compare outcomes of one subset of her patients against a different subset of her patients, or compare outcomes of her pediatric patients against a group of teenage patients that include her patients and teenage patients under the care of non-customer HCPs). Although the system accommodates end user selection or designation of the patient attributes, the system may also utilize predefined patient groups (sets of attributes) to lessen the amount of input that is required of the customer HCP.

This example assumes that the patient therapy management system receives a first set of attributes for a first individual patient (or a first group of patients) under the care of the customer HCP (task 404), and a second set of attributes for a second individual patient (or a second group of patients (task 406). In certain implementations of the system, the first set of patient attributes and the second set of patient attributes are received from a client device associated with the customer HCP, such as a computer that is owned or operated by the customer HCP. For example, the process 400 may provide a suitably configured therapy management website in a web browser running on the customer HCP's computer, wherein a page or interactive element of the website facilitates the entry, selection, or designation of the first and second sets of patient attributes.

Although the system and the process 400 are not limited to diabetes applications, the embodiment presented here assumes that the medical device users are diabetic patients using insulin infusion devices. Accordingly, the first/second set of patient attributes may include one or more of the following attributes, without limitation: a patient age attribute; a patient gender attribute; a patient height attribute; a patient weight attribute; a geographic location attribute; a time attribute that indicates how long a patient has been on insulin therapy; and an onset age attribute that indicates how old a patient was at the onset of diabetes. Patients can also be grouped based on diabetes type, medication type, adherence to medication, comorbidities, body mass index, A1C score, glycemic outcomes, glucose response to specific events, lifestyle, insurance payors, and any other clinical or device-specific training programs in which they are participating. In addition, machine learning techniques such as supervised or unsupervised clustering can be used to group patients based on complex underlying patterns. It should be appreciated that the patient attributes utilized for any given deployment of the system may vary depending on the medical device(s) under consideration, the medical condition(s) being treated, HCP preferences, patient demographics, etc. The above listing of attributes is suitable for the example discussed here, and is not intended to limit or restrict the scope of applicability of the disclosed subject matter in any way.

In some situations, the first set of attributes match the second set of attributes such that the process 400 performs an "apples to apples" comparison of similar groups of patients. In those situations, the process 400 need not redundantly receive two sets of attributes. In other scenarios, however, the first set of attributes do not match the second set of attributes (at least one attribute is different). This allows the customer HCP to compare one or more of his patients against any desired group of other patients. For example, the customer HCP may be interested in comparing the outcomes of his female middle-aged patients (who all live in San Diego, Calif.) against the outcomes of a population of male teenage patients (regardless of residence). In practice, therefore, the system and the process 400 flexibly accommodate grouping of patients in any desired manner. As another example, the process 400 may receive the first set of attributes, and "create" the second set of attributes based on the first set of attributes, wherein the second set of attributes can match the first set of attributes or depart from the first set of attributes in any desired way.

The process 400 utilizes the patient attributes to search for and identify corresponding patient records (from the collected patient data) that satisfy the patient attributes. To this end, the process 400 identifies a first set of patient records associated with the customer HCP, wherein the identified patient records satisfy the first set of attributes (task 408). Similarly, the process 400 identifies a second set of patient records associated with the customer HCP, wherein those identified patient records satisfy the second set of attributes (task 410). Accordingly, the process 400 finds the relevant patient records (patient data) to be compared against each other.

In accordance with a use case where the first and second sets of attributes are similar or identical, the process 400 compares patient outcomes, results, and/or other information from the identified first set of patient records against patient outcomes, results, and/or other information from the identified second set of patient records (task 412). The process 400 continues by determining (based on the comparison) whether or not there is a clinically significant difference between the patient outcomes from the identified first set of patient records and the patient outcomes from the identified second set of patient records (task 414).

This description assumes that the process 400 detects a difference between the patient outcomes. In response to such a determination, the process 400 analyzes at least the identified first set of patient records in an attempt to find potential causes of the detected difference (task 416). In this regard, one or more factors may be found to be a cause of the different outcomes. For example, any of the following may influence different outcomes between patients or groups of patients, without limitation: medical device settings or therapy delivery settings; analyte sensor settings or performance characteristics; patient behavior; medication type; and therapy regimen. Depending on the particular implementation of the system, the process 400 can apply autoregressive, curve fitting, data filtering, data conditioning, and/or other statistical models or techniques on the patient records and patient data to determine causation. The goal of task 416 is to identify the reasons why the clinical outcomes of one group of patients (e.g., the customer HCP's patients) are statistically different than the clinical outcomes of a second group of patients. The system and methodology described here leverages a potentially vast amount of population-based patient data to enable the customer HCP to get a better sense of how her patients compare against other patients, and to discover ways to improve the care of her patients.

The process 400 continues by generating suitably configured and formatted comparative therapy output for presentation to the customer HCP (task 418). For this particular example, the process 400 generates a report, a recommendation, a message, instructions, and/or a medical device control command that indicates or is otherwise related to the results of the comparison. In practice, a comparative therapy report can include or indicate: the potential causes of a clinically significant difference in patient outcomes; a therapy adjustment recommendation; a medical device adjustment recommendation; a patient behavioral change recommendation; a medication change recommendation; a graphical representation of patient data; a graphical representation of patient outcomes; statistical information that reflects the comparison of the patient records; and the like.

The process 400 continues by communicating the comparative therapy output (report) to a client device that is associated with, owned by, or operated by the customer HCP (task 420). For this particular example, the therapy management system and the process 400 provide a therapy management website to the customer HCP's device, and the therapy management website includes at least one webpage that contains the comparative therapy report. In other implementations, the output can be communicated in any desired fashion, such as by email, a text message, a customized application or software, a private message, or the like.

Although not always required or necessary, the output may include an active element, a feature, and/or appropriate functionality that facilitates the automatic adjustment of at least one medical device in accordance with a therapy adjustment recommendation. For example, a displayed comparative therapy report may include a suggestion (intended for the customer HCP) to adjust a setting of the patient's medical device. The report may be displayed in combination with an active user interface button or link that, when selected by the customer HCP, initiates, commands, or otherwise causes the automatic adjustment of the patient's medical device in an appropriate manner (task 422). This option assumes that the patient's medical device is in operative communication with the HCP's client device and/or with the patient therapy management system (see, FIG. 1 as an example).

Figure 5:
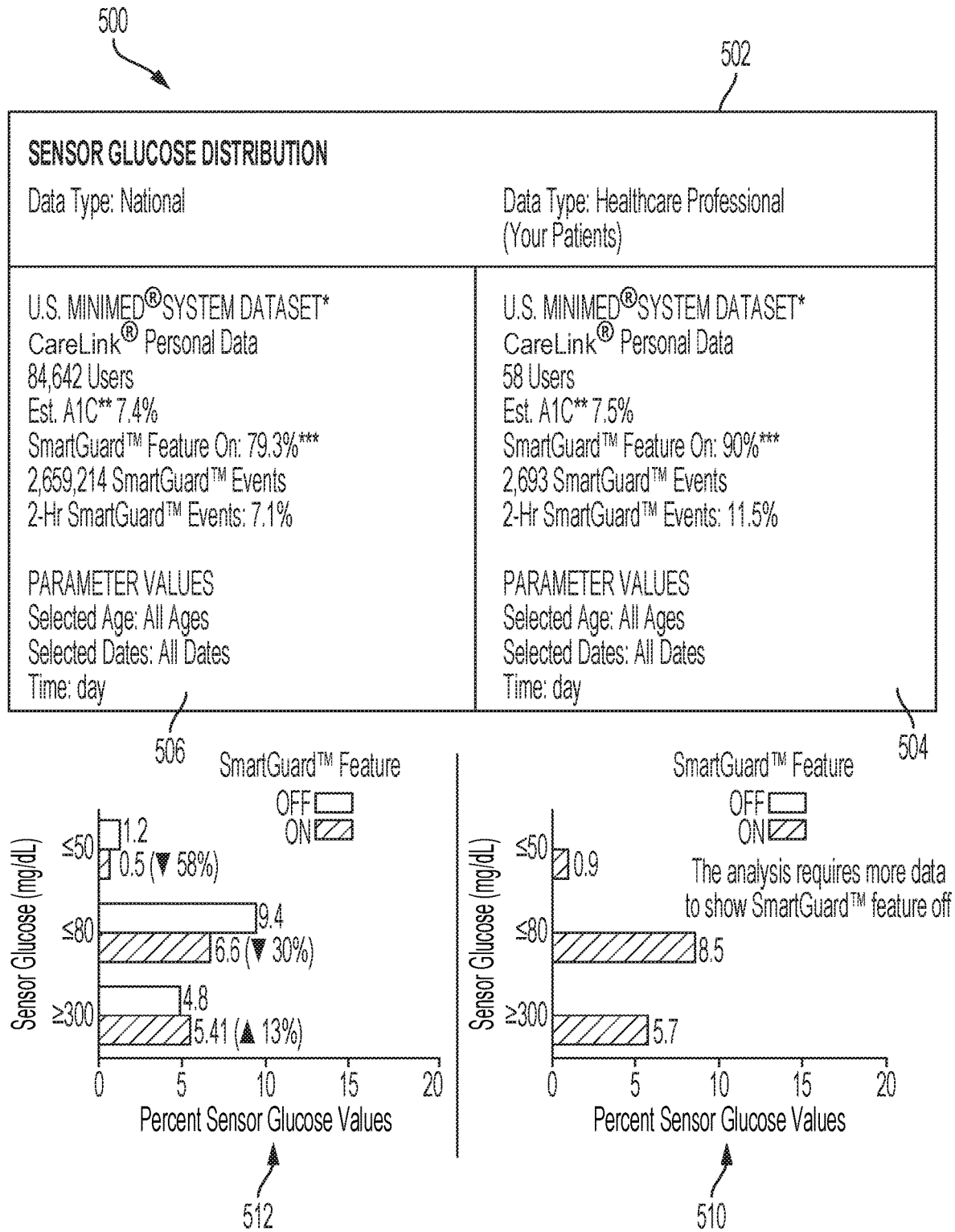
FIG. 5 is a diagram of a sensor glucose distribution report.
Figure 6:
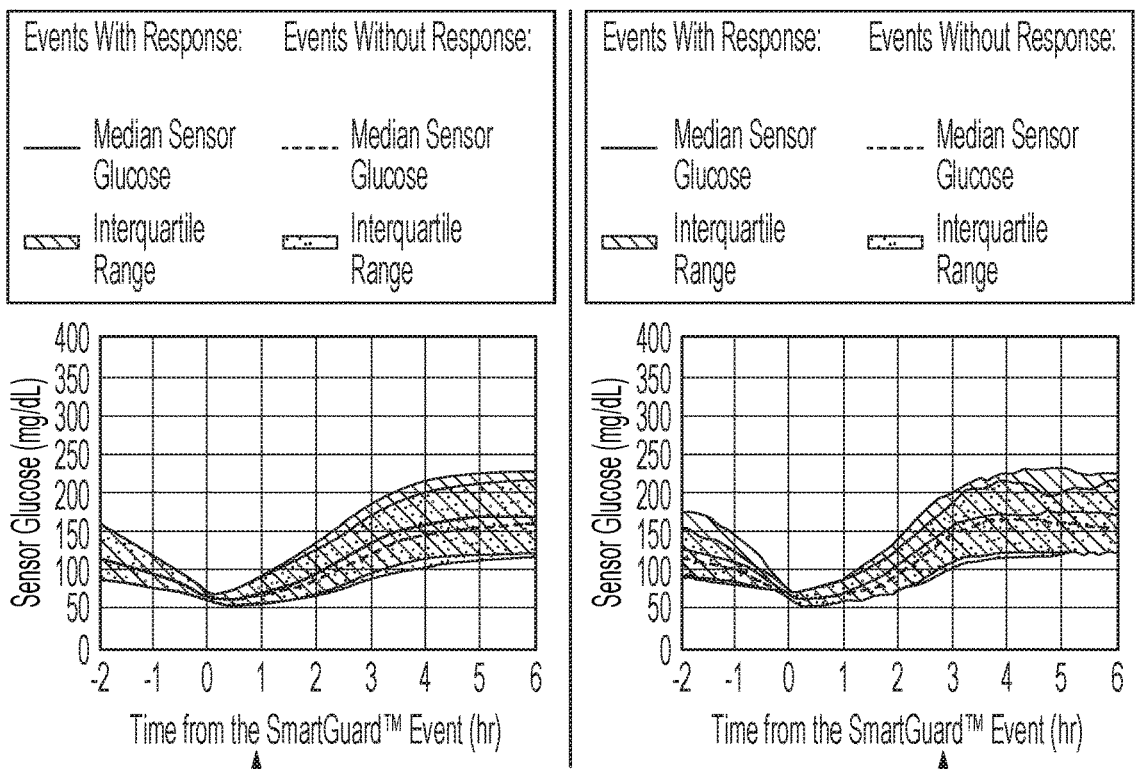
FIG. 6 is a diagram of a glucose recovery report.

FIG. 5 is a diagram of a sensor glucose distribution report 500, and FIG. 6 is a diagram of a glucose recovery report 600. These reports 500, 600 are two examples of the type of comparative output that can be generated and delivered by the system described above. The report 500 generally includes a patient attribute and data region 502, which is divided into a customer HCP zone 504 and a comparative HCP zone 506. The depicted report 500 compares the customer HCP's patients against a nationwide population of other patients (as indicated by the "Data Type" fields). The customer HCP zone 504 shows at least some of the attributes that have been used to define the customer HCP's patients under review. These attributes are listed under the heading "Parameter Values" in the customer HCP zone 504. Similarly, the comparative HCP zone 506 shows at least some of the attributes that have been used to define the group of other patients that serve as the basis for comparison against the customer HCP's patients. These attributes are listed under "Parameter Values" in the comparative HCP zone 506. For this example, the attributes for both groups of patients are the same.

The customer HCP zone 504 also includes certain information related to the customer HCP's patients. For example, the customer HCP zone 504 indicates that 58 patients (users) were considered, the estimated A1C score for the group of patients is 7.5%, an automated therapy delivery mode (SmartGuard) was active 90% of the time, 2,693 SmartGuard events were recorded, and two-hour SmartGuard events were 11.5%. The SmartGuard feature in the pump suspends glucose delivery when the patient's glucose level crosses the low threshold. This feature helps to reduce the duration of low glycemic excursions. The statistics indicate that for the 58 patients, there were 2,693 instances when the SmartGuard feature suspended the insulin delivery and the insulin was suspended for more than two hours for only 11.5% of these total instances. This implies that for the remaining SmartGuard events, the patients would have taken remedial actions (e.g., consume carbohydrates or stop exercising) to avoid prolonged low glucose excursions. Similarly, The comparative HCP zone 506 includes certain information related to the other group of patients. For this example, the comparative HCP zone 506 indicates that 84,642 patients (users) were considered, the estimated A1C score for that group of patients is 7.4%, the SmartGuard mode was active 79.3% of the time, 2,659,214 SmartGuard events were recorded, and two-hour SmartGuard events were 7.1%. These are population level insights. The statistics indicate that for the 84,642 patients, there were 2,659,214 instances when the SmartGuard feature suspended insulin delivery and the insulin was suspended for more than two hours for only 7.1% of these total instances.

The report 500 also includes a sensor glucose graphic 510 for the customer HCP's patients, and an equivalent sensor glucose graphic 512 for the other group of patients. These graphics 510, 512 include data for three sensor glucose ranges (shown on the vertical scale), wherein the horizontal scale represents the percentage of time the patients were measured to be within the respective ranges. The graphic 512 includes two bar graphs per sensor glucose range: one corresponding to measurements with the SmartGuard mode on, and one corresponding to measurement with the SmartGuard mode off. The graphic 510 indicates that there is not enough patient data with the SmartGuard mode off. Consequently, the graphic 510 only shows one bar graph per sensor glucose range. The customer HCP can quickly and easily view the graphics 510, 512 in the context of the information presented in the zones 505, 506 to obtain a good sense of how the customer HCP's patients compare to the large nationwide group of patients.

With reference to FIG. 6, the report 600 also includes a patient attribute and data region 602, which is divided into a customer HCP zone 604 and a comparative HCP zone 606. The depicted report 600 compares the customer HCP's patients against a nationwide population of other patients (as indicated by the "Data Type" fields). The zones 604, 606 include patient attributes listed under the "Parameter Values" headings. The customer HCP zone 604 also includes certain information related to the customer HCP's patients. For example, the customer HCP zone 604 indicates that 58 patients (users) were considered, there were 597 SmartGuard events with a user response, and there were 182 SmartGuard events without a user response. Similarly, The comparative HCP zone 606 includes certain information related to the other group of patients. For this example, the comparative HCP zone 606 indicates that 84,642 patients (users) were considered, there were 423,264 SmartGuard events with a user response, and there were 223,432 SmartGuard events without a user response.

The report 600 also includes a sensor glucose "swoosh" graphic 610 for the customer HCP's patients, and an equivalent sensor glucose "swoosh" graphic 612 for the other group of patients. These graphics 610, 612 include sensor glucose measurement data relative to the timing of an SmartGuard event, i.e., an insulin suspension event that is associated with the consumption of a meal at time t=0. The customer HCP can quickly and easily view the graphics 610, 612 in the context of the information presented in the zones 604, 606 to obtain a good sense of how the customer HCP's patients compare to the large nationwide group of patients. Although not shown in FIG. 6, the report 600 may also include a recommendation regarding how much carbohydrate the patient(s) should consume, and when, to improve results.

FIG. 5 and FIG. 6 are provided here to illustrate the format and arrangement of two output reports. It should be appreciated that the reports 500, 600 represent only two possible forms of output that can be generated by the patient therapy management system described here. A variety of additional or alternative reports, created in different formats and layouts, can be generated and presented to the customer HCPs if so desired. As mentioned above, the system can provide a website for navigation and interaction by the customer HCP, wherein the customer HCP can initiate the rendering of different reports, output formats, statistics, and the like.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method of generating and communicating comparative therapy information for medical device users, the method comprising the steps of:
collecting patient data associated with a plurality of medical device users, wherein treatment of the medical device users is managed by a plurality of healthcare professionals (HCPs), and the plurality of HCPs comprises a customer HCP and a plurality of non-customer HCPs;
receiving a first set of attributes for a first individual patient or a first group of patients under care of the customer HCP;
receiving a second set of attributes for a second individual patient or a second group of patients;
identifying, from the collected patient data, a first set of patient records associated with the customer HCP that satisfy the received first attributes;
identifying, from the collected patient data, a second set of patient records that satisfy the received second attributes;
analyzing aggregated patient data for the first set of patient records to generate a first set of one or more statistics related to medical device usage;
analyzing aggregated patient data for the second set of patient records to generate a second set of one or more statistics related to medical device usage;
comparing the first set of one or more statistics from the identified first set of patient records against the second set of one or more statistics from the identified second set of patient records to detect a difference between patient outcomes;
in response to detecting the difference between patient outcomes, analyzing the first set of patient records to identify a medical device setting as a cause of the difference between the patient outcomes;
generating a comparative therapy report that indicates results of the comparing step, wherein the comparative therapy report indicates the medical device setting as the cause of the difference between the patient outcomes;
communicating, over a data communication network, a web page including the comparative therapy report to a client device associated with the customer HCP, wherein the comparative therapy report includes a therapy adjustment suggestion to adjust the medical device setting for the first individual patient or the first group of patients; and initiating, over the data communication network, automatic adjustment of the medical device setting for the first individual patient or the first group of patients in response to the customer HCP selecting an active user interface button or link displayed in combination with the therapy adjustment suggestion on the comparative therapy report.

2. The method of claim 1, wherein:
the medical device users are insulin infusion device users; and
the patient data comprises at least some of: carbohydrate amount; bolus information; insulin to carbohydrate ratio; insulin sensitivity factor; active insulin amount; time of day; basal rate; temporary basal use; consecutive boluses; insulin suspension; reservoir rewind time; reservoir priming time; pump alarms and associated alarm times; sensor alerts and associated alert times; blood glucose readings and associated measurement times; user demographic information; meal times and corresponding meal content; exercise times and corresponding exercise content or type; medication type, dosage, and time; sleep time and quality; stress time; and electronic medical records; medical lab test data.

3. The method of claim 1, wherein the first set of attributes and the second set of attributes are received from the client device associated with the customer HCP.

4. The method of claim 1, wherein the medical device users are diabetic patients using insulin infusion devices, and wherein the first set of attributes comprises one or more of the following attributes:
a patient age attribute;
a patient gender attribute;
a patient height attribute;
a patient weight attribute;
a geographic location attribute;
a time attribute that indicates how long a patient has been on insulin therapy;
an onset age attribute that indicates how old a patient was at the onset of diabetes.

5. The method of claim 1, wherein the medical device users are diabetic patients using insulin infusion devices, and wherein the second set of attributes comprises one or more of the following attributes:
a patient age attribute;
a patient gender attribute;
a patient height attribute;
a patient weight attribute;
a geographic location attribute;
a time attribute that indicates how long a patient has been on insulin therapy; and
an onset age attribute that indicates how old a patient was at the onset of diabetes.

6. The method of claim 1, wherein the first set of attributes match the second set of attributes.

7. The method of claim 1, wherein:
the second set of attributes is received for a second individual patient or a second group of patients under care of at least one of the non-customer HCPs; and
the second set of patient records is associated with at least one of the non-customer HCPs.

8. The method of claim 1, wherein:
the comparative therapy report indicates a medical device adjustment recommendation that reflects the comparing the first set of one or more statistics from the identified first set of patient records against the second set of one or more statistics from the identified second set of patient records.

9. The method of claim 8, wherein:
identifying the first set of patient records comprises identifying the first set of patient records that satisfy a first state for the medical device setting comprising an automated therapy delivery mode;
identifying the second set of patient records comprises identifying the second set of patient records that satisfy a second state for the medical device setting comprising the automated therapy delivery mode; and
the comparative therapy report indicates the medical device setting causing the difference between patient outcomes.

10. The method of claim 9, wherein the medical device comprises an insulin infusion device and the automated therapy delivery mode suspends glucose delivery when a patient's glucose level crosses a low threshold.

11. The method of claim 1, wherein the medical device setting comprises an automated therapy delivery mode.

12. The method of claim 11, wherein the cause of the difference comprises the automated therapy delivery mode being enabled or activated.

13. The method of claim 12, wherein the medical device comprises an insulin infusion device and the automated therapy delivery mode suspends glucose delivery when a patient's glucose level crosses a low threshold.

14. The method of claim 11, wherein the medical device comprises an insulin infusion device and the automated therapy delivery mode suspends glucose delivery when a patient's glucose level crosses a low threshold.

15. The method of claim 1, wherein the medical device comprises an infusion device or a continuous glucose sensor device.

16. A computer-implemented therapy management system comprising:
at least one processor device; and
a non-transitory processor-readable medium operatively associated with the at least one processor device, the processor-readable medium comprising executable instructions configurable to cause the at least one processor device to perform a method comprising:
collecting patient data associated with a plurality of medical device users, wherein treatment of the medical device users is managed by a plurality of healthcare professionals (HCPs), and the plurality of HCPs comprises a customer HCP and a plurality of non-customer HCPs;
receiving a first set of attributes for a first individual patient or a first group of patients under care of the customer HCP;
receiving a second set of attributes for a second individual patient or a second group of patients;
identifying, from the collected patient data, a first set of patient records associated with the customer HCP that satisfy the received first attributes;
identifying, from the collected patient data, a second set of patient records that satisfy the received second attributes;
analyzing aggregated patient data for the first set of patient records to generate a first set of one or more statistics related to medical device usage;
analyzing aggregated patient data for the second set of patient records to generate a second set of one or more statistics related to the medical device usage;
comparing the first set of one or more statistics from the identified first set of patient records against the second set of one or more statistics from the identified second set of patient records to detect a difference between patient outcomes;

in response to detecting the difference between patient outcomes, analyzing the first set of patient records to identify a medical device setting as a cause of the difference between the patient outcomes;

generating a comparative therapy report that indicates results of the comparing step, wherein the comparative therapy report indicates the medical device setting as the cause of the difference between the patient outcomes;

communicating, over a data communication network, a web page including the comparative therapy report to a client device associated with the customer HCP, wherein the comparative therapy report includes a therapy adjustment suggestion to adjust the medical device setting for the first individual patient or the first group of patients; and initiating, over the data communication network, automatic adjustment of the medical device setting for the first individual patient or the first group of patients in response to the customer HCP selecting an active user interface button or link displayed in combination with the therapy adjustment suggestion on the comparative therapy report.

17. The system of claim 16, wherein the medical device users are diabetic patients using insulin infusion devices, and wherein the attributes comprise one or more of the following attributes:
- a patient age attribute;
- a patient gender attribute;
- a patient height attribute;
- a patient weight attribute;
- a geographic location attribute;
- a time attribute that indicates how long a patient has been on insulin therapy;
- an onset age attribute that indicates how old a patient was at the onset of diabetes.

18. A system comprising:
a computer-implemented therapy management system;
a database system, associated with the therapy management system, to collect and maintain patient data associated with a plurality of medical device users, wherein treatment of the medical device users is managed by a plurality of healthcare professionals (HCPs), and the plurality of HCPs comprises a customer HCP and a plurality of non-customer HCPs; and
a computer-implemented user device communicatively coupled to the therapy management system, the user device associated with the customer HCP;
the therapy management system operative to:
receive a first set of attributes for a first individual patient or a first group of patients under care of the customer HCP;
receive a second set of attributes for a second individual patient or a second group of patients;
identify, from the collected patient data, a first set of patient records associated with the customer HCP that satisfy the received first attributes;
identify, from the collected patient data, a second set of patient records that satisfy the received second attributes;
analyze aggregated patient data for the first set of patient records to generate a first set of one or more statistics related to at least one of patient behavior, medical device usage;
analyze aggregated patient data for the second set of patient records to generate a second set of one or more statistics related to the medical device usage;
compare the first set of one or more statistics from the identified first set of patient records against the second set of one or more statistics from the identified second set of patient records to detect a difference between patient outcomes;
in response to detecting the difference between patient outcomes, analyze the first set of patient records to identify a medical device setting as a cause of the difference between the patient outcomes;
generate a comparative therapy report that indicates results of the comparing step, wherein the comparative therapy report indicates the medical device setting as the cause of the difference between the patient outcomes;
communicate, over a data communication network, a web page including the comparative therapy report to the user device associated with the customer HCP, wherein the comparative therapy report includes a therapy adjustment suggestion to adjust the medical device setting for the first individual patient or the first group of patients; and
initiate, over the data communication network, automatic adjustment of the medical device setting for the first individual patient or the first group of patients in response to the customer HCP selecting an active user interface button or link displayed in combination with the therapy adjustment suggestion on the comparative therapy report.

19. The system of claim 18, wherein the first set of attributes and the second set of attributes are received from the user device associated with the customer HCP.

20. The system of claim 18, wherein:
the therapy management system provides a therapy management website to the user device; and
the therapy management website comprises at least one webpage that includes the comparative therapy report.

* * * * *